United States Patent [19]

Ebata et al.

[11] Patent Number: 5,064,768

[45] Date of Patent: Nov. 12, 1991

[54] SILVER STAINING TECHNIQUE AND KIT

[75] Inventors: Nobuyoshi Ebata; Yuko Tanaka; Akiko Negishi, all of Tokyo, Japan

[73] Assignee: Daiichi Pure Chemicals Co., Ltd., Tokyo, Japan

[21] Appl. No.: 405,479

[22] Filed: Sep. 12, 1989

[30] Foreign Application Priority Data

Sep. 16, 1988 [JP] Japan ................................ 63-232058
Sep. 16, 1988 [JP] Japan ................................ 63-232059

[51] Int. Cl.[5] ...................... G01N 21/77; G01N 33/68

[52] U.S. Cl. ...................................... 436/164; 422/61; 436/86; 436/94; 436/169; 436/905

[58] Field of Search .................................... 436/86–88, 436/94, 164, 169, 174, 175, 177, 178, 905; 422/61

[56] References Cited

U.S. PATENT DOCUMENTS

| | | | |
|---|---|---|---|
| 4,468,466 | 8/1984 | Morrissey | 436/86 |
| 4,554,254 | 11/1985 | Krystal | 436/86 |
| 4,575,452 | 3/1986 | Lee et al. | 422/61 |
| 4,582,808 | 4/1986 | Oosawa et al. | 436/86 |
| 4,690,901 | 9/1987 | Giammara et al. | 436/86 |
| 4,703,016 | 10/1987 | Merril | 422/61 X |

OTHER PUBLICATIONS

Giulian et al, Anal. Biochem., vol. 129, No. 2, pp. 277–287, 1983.

*Primary Examiner*—Robert J. Hill, Jr.
*Attorney, Agent, or Firm*—Oblon, Spivak, McClelland, Maier & Neustadt

[57] ABSTRACT

An improved silver staining technique is disclosd for the detection of a biocomponent contained in a support medium. The technique includes fixing the support medium with a fixing agent, pretreating the thus-fixed support medium with a sensitizer, treating the resultant support medium with a silver staining solution and then developing the thus-treated support medium with a reducing agent. In one aspect of the invention, thiourea is incorporated in either one or both of the fixing agent and sensitizer. In another aspect of the invention, thiosulfate is contained in the reducing agent. According to the invention, improved stainability and contrast are obtained. Also disclosed is a silver staining kit.

16 Claims, 6 Drawing Sheets

SILVER STAINING TECHNIQUE AND KIT

BACKGROUND OF THE INVENTION i) Field of the Invention

This invention relates to an improvement in silver staining technique for detecting one or more biocomponents fractionated on a support medium in electrophoresis or the like, such as proteins, nucleic acids, saccharides and/or lipids.

ii) Description of the Background Art

Silver staining technique is a method for detecting a substance (hereinafter called a "target substance") by treating a support medium,. which contains the target substance, with a fixing agent to fix the target substance, pretreating the support medium, treating the pretreated support medium with a silver staining solution and then developing the thus-treated support medium with a reducing agent. It can analyze low-concentration samples of one or more target substances such as proteins, nucleic acids, saccharides and/or lipids, i.e., serum, urine, cerebrospinal fluid and the like without need for concentration, and is a useful analytical method employed widely in biochemical research, clinical tests, etc.

A wide variety of methods have been reported for achieving silver staining, for example, in "Seikagaku", 52, 411 (1980), "Tanpakushitsu, Kakusan, Koso", 27, 1277 (1982), "Electrophoresis", 2, 135, 141 (1981). All of these methods, however, require a long time and/or irksome procedures until completion of staining. Further, the silver-stained profiles thus obtained involve many problems such as (1) the stainability varies depending on the substance to be stained, (2) no complete staining is feasible for high-concentration samples, and (3) the contrast is low due to staining of the background. Accordingly, there has been a longstanding desire for the development of an improved silver staining technique.

SUMMARY OF THE INVENTION

The present inventors have therefore conducted an extensive investigation with a view toward solving such problems, specifically in order to shorten the operation time of the silver staining technique, to improve the staining ability and also to improve the contrast. As a result, it has been found that (1) the silver ions in a silver staining solution can be easily reduced in the presence of thiourea and moreover blackening of the thus-reduced silver can be enhanced owing to sulfurized sensitization by thiourea and (2) addition of a thiosulfate to a reducing agent can solubilize free silver ions on a support medium to prevent staining of the support medium, thereby providing stained bands of improved contrast after development, leading to the completion of this invention.

In one aspect of this invention, there is thus provided a silver staining technique comprising fixing a support medium, which contains a substance to be detected, with a fixing agent, pretreating the thus-fixed support medium with a sensitizer, treating the resultant support medium with a silver staining solution and then developing the thus-treated support medium with a reducing agent. A principal feature of this invention resides in that thiourea is incorporated in at least one of the fixing agent and sensitizer. In another aspect of this invention, there is also provided a silver staining kit useful in the practice of the silver staining technique.

In a further aspect of this invention, there is also provided a silver staining technique comprising fixing a support medium, which contains a substance to be detected, with a fixing agent, pretreating the thus-fixed support medium with a sensitizer, treating the resultant support medium with a silver staining solution and then developing the thus-treated support medium with a reducing agent. Another principal feature of this invention resides in that a thiosulfate is incorporated in the reducing agent. In a still further aspect of this invention, there is also provided a silver staining kit useful in the practice of the silver staining technique.

Figure 1:
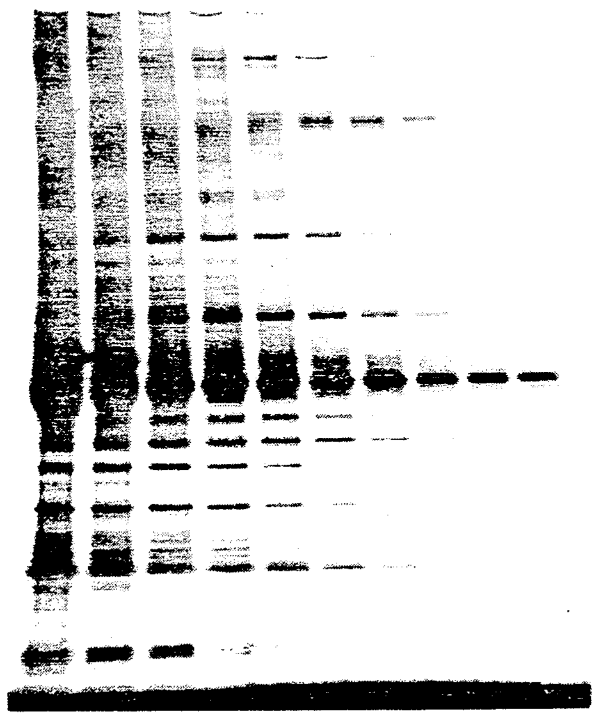
FIG. 1 (PRIOR ART) is a photograph of a silver-stained electrophoretic profile obtained by a comparative technique.
Figure 2:
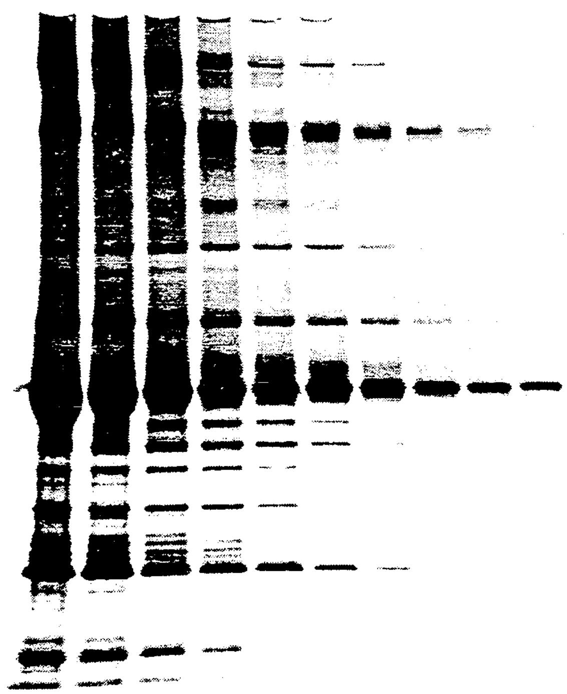
FIG. 2 is a photograph of a silver-stained electrophoretic profile obtained by the technique of Example 1.
Figure 3:
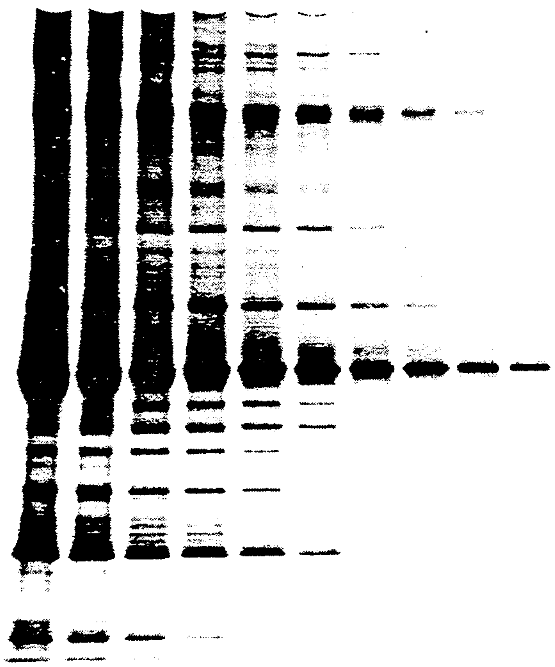
FIG. 3 is a photograph of a silver-stained electrophoretic profile obtained by the technique of Example 2.
Figure 4:
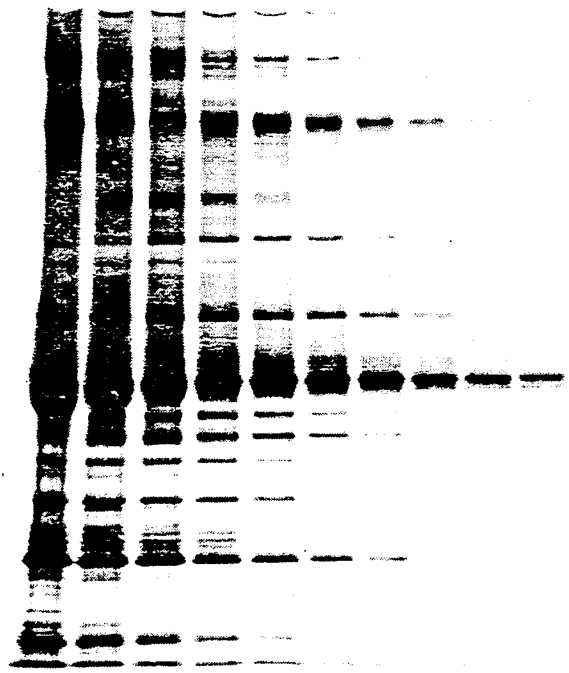
FIG. 4 is a photograph of a silver-stained electrophoretic profile obtained by the technique of Example 3.
Figure 5:
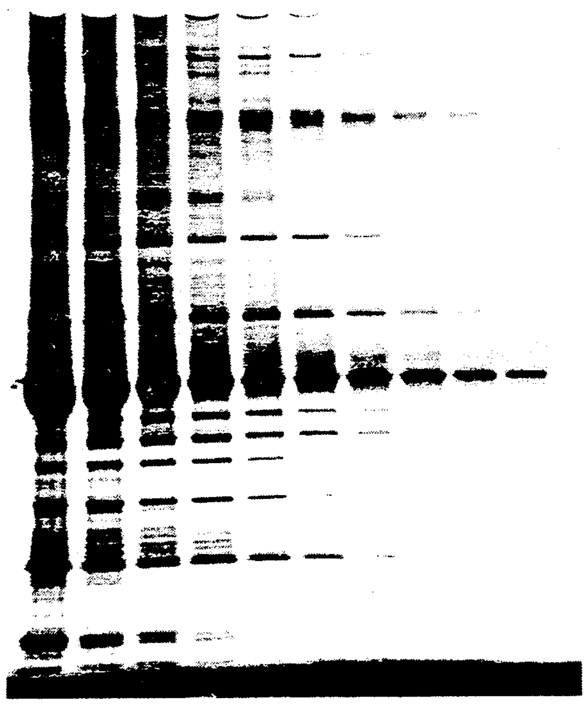
FIG. 5 is a photograph of a silver-stained electrophoretic profile obtained by the technique of Example 20.
Figure 6:
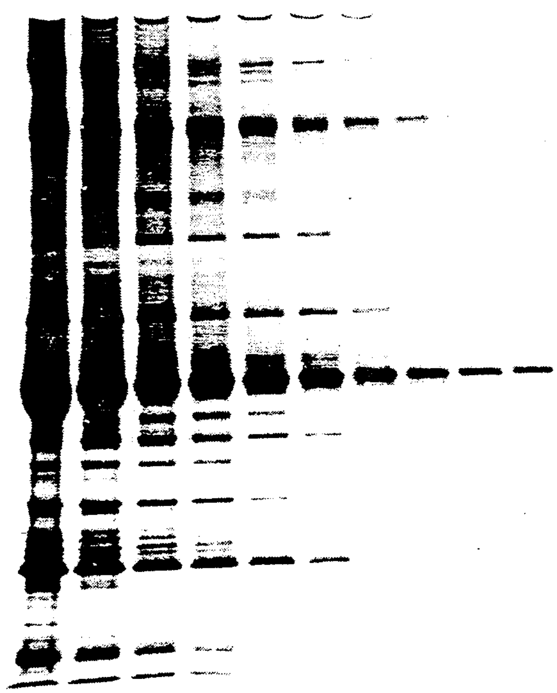
FIG. 6 is a photograph of a silver-stained electrophoretic profile obtained by the technique of Example 25.

In each of drawings, the individual bands correspond, in the rightward direction, to a normal human serum sample diluted fiftyfold in water, and 2-fold, 4-fold, 8-fold, 16-fold, 32-fold, 64-fold, 128-fold, 256-fold and 512-fold dilute aqueous solutions of the fifty fold-diluted serum sample, respectively.

DETAILED DESCRIPTION OF THE INVENTION AND PREFERRED EMBODIMENTS

Preferred examples of the fixing agent useful in the practice of the silver staining technique according to this invention include those containing a lower alcohol having 1–4 carbon atoms and an organic acid. Illustrative lower alcohols having 1–4 carbon atoms include methyl alcohol, ethyl alcohol, n-propyl alcohol, isopropyl alcohol, n-butyl alcohol, isobutyl alcohol, secondary butyl alcohol, and tertiary butyl alcohol. Exemplary useful organic acids are led by monobasic acids such as acetic acid and propionic acid and include dibasic acids such as succinic acid and tartaric acid and tribasic acids such as citric acid.

When thiourea is incorporated in the fixing agent, its concentration may be at least 0.00001 w/v%. However, a concentration of 0.001–0.1 w/v% is preferred in general. Although no particular limitation is imposed on the concentration of the alcohol in the fixing agent, a concentration of 10–60 v/v% is preferred in general. On the other hand, the concentration of the organic acid may be at least 5 w/v% but a range of 10–30 w/v% is preferred in general.

The fixing treatment may be applied only once with a solution which contains thiourea, a lower alcohol and an organic acid. It is however preferable to conduct it in two stages, for example, (i) first treating with a first fixing agent composed of the lower alcohol and organic acid and then with a second fixing agent composed of thiourea, the lower alcohol and the organic acid, (ii)

first treating with a first fixing agent composed of thiourea, the lower alcohol and the organic acid and then with a second fixing agent composed of the lower alcohol and organic acid, or (iii) dividing into two portions a fixing agent composed of thiourea, the lower alcohol and the organic acid and conducting the same procedure twice. In these two-stage treatments, it is usually desired that the alcohol concentration in the first fixing agent is higher than that in the second fixing agent. As the immersion time for the fixing treatment about 10 minutes is sufficient for the first fixing and about 15 minutes for the second fixing.

As the sensitizer useful for the pretreatment in the technique of this invention, one containing dithiothreitol and glutaraldehyde may be mentioned by way of example.

When thiourea is incorporated in the sensitizer, its concentration may range from 0.00001 w/v% to 0.01 w/v%. However, a concentration of 0.0002-0.0005 w/v% is preferred in general. Although not limited particularly, a concentration of 0.0002-0.002 w/v% may be used preferably. On the other hand, the concentration of glutaraldehyde may be at least 0.005 w/v% but a range of 0.005-0.2 w/v% is preferred in general.

The pretreatment can be conducted by immersing the support medium, which has been fixed with the fixing agent, in the sensitizer solution. About 10 minutes is sufficient as this immersion time.

Although not limited particularly, the silver staining solution employed in this invention may preferably contain, for example, silver nitrate, a compound represented by R-$NH_2$ wherein R denotes a hydrogen atom or a monovalent hydrocarbyl group, i.e., ammonia or a primary amine such as methylamine, ethanolamine, etc., and a caustic alkali such as NaOH, KOH, etc., at a molar ratio of 1 : 4.5-9.5 : 1.0-26.0. Although no particular limitation is imposed on the concentration of silver nitrate either, 0.05-0.4 w/v% is preferred in general.

The silver staining treatment is conducted by immersing the support medium, which has been subjected to the fixing and sensitizing treatments, in the silver staining solution. Ten to fifteen minutes is sufficient as the immersion time.

Any reducing agent may be used in the silver staining technique of this invention so long as it has reducing ability for silver ions. As preferred reducing agents, may be mentioned those containing formaldehyde and citric acid.

As thiosulfates which may be incorporated in the reducing agent, may be mentioned sodium thiosulfate, ammonium thiosulfate and the like. Of these, sodium thiosulfate is preferred.

When sodium thiosulfate is incorporated in the reducing agent, its concentration may be at least 0.000005 w/v% with 0.00002-0.001 w/v% being preferred in particular. Where the reducing agent contains formaldehyde and citric acid, the concentration of formaldehyde may generally be 0.001 w/v% with 0.01-0.04 w/v% being preferred. On the other hand, the concentration of citric acid may be 0.0005 w/v% or higher with about 0.002-0.01 w/v% being preferred. The weight ratio of formaldehyde to citric acid may preferably be 1:0.25-0.5.

Five to 10 minutes is sufficient as the developing time when the development is conducted using the above reducing agent.

Incidentally, typical examples of the support medium employed in this invention may include those composed of high-molecular carriers having a network structure in general, such as polyacrylamide gels, agarose gels and agar gels.

The technique of this invention can be practiced in a manner similar to conventional silver staining techniques except that thiourea is incorporated in either one or both of the fixing agent and sensitizer or a thiosulfate is incorporated in the reducing agent.

Upon practice of the technique of this invention, it is preferred. for example, to use either one of the following kits A-G:

A. A silver staining kit comprising:

i) a fixing agent comprising a lower alcohol having 1-4 carbon atoms, an organic acid and thiourea;

ii) a sensitizer comprising dithiothreitol and glutaraldehyde;

iii) a silver staining solution comprising silver nitrate, a compound represented by R-$NH_2$ wherein R denotes a hydrogen atom or a monovalent hydrocarbyl group, and a caustic alkali; and iv) a reducing agent comprising formaldehyde and citric acid.

B. A silver staining kit comprising:

i) a fixing agent comprising a lower alcohol having 1-4 carbon atoms and an organic acid;

ii) a sensitizer comprising dithiothreitol, glutaraldehyde and thiourea;

iii) a silver staining solution comprising silver nitrate, a compound represented by R-$NH_2$ wherein R denotes a hydrogen atom or a monovalent hydrocarbyl group, and a caustic alkali; and iv) a reducing agent comprising formaldehyde and citric acid.

C. A silver staining kit comprising:

i) a fixing agent comprising a lower alcohol having 1-4 carbon atoms, an organic acid and thiourea;

ii) a sensitizer comprising dithiothreitol, glutaraldehyde and thiourea;

iii) a silver staining solution comprising silver nitrate, a compound represented by R-$NH_2$ wherein R denotes a hydrogen atom or a monovalent hydrocarbyl group, and a caustic alkali; and iv) a reducing agent comprising formaldehyde and citric acid.

D. A silver staining kit comprising:

i) a fixing agent comprising a lower alcohol having 1-4 carbon atoms and an organic acid;

ii) a sensitizer comprising dithiothreitol and glutaraldehyde;

iii) a silver staining solution comprising silver nitrate, a compound represented by R-$NH_2$ wherein R denotes a hydrogen atom or a monovalent hydrocarbyl group, and a caustic alkali; and iv) a reducing agent comprising a thiosulfate.

E. A silver staining kit comprising:

i) a fixing agent comprising a lower alcohol having 1-4 carbon atoms, an organic acid and thiourea;

ii) a sensitizer comprising dithiothreitol and glutaraldehyde;

iii) a silver staining solution comprising silver nitrate, a compound represented by R-$NH_2$ wherein R denotes a hydrogen atom or a monovalent hydrocarbyl group, and a caustic alkali; and iv) a reducing agent comprising a thiosulfate.

F. A silver staining kit comprising:

i) a fixing agent comprising a lower alcohol having 1-4 carbon atoms and an organic acid;

ii) a sensitizer comprising dithiothreitol, glutaraldehyde and thiourea;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising a thiosulfate.

G. A silver staining kit comprising:

i) a fixing agent comprising a lower alcohol having 1–4 carbon atoms, an organic acid and thiourea;

ii) a sensitizer comprising dithiothreitol, glutaraldehyde and thiourea;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising a thiosulfate.

As has been described above, this invention has provided an improvement in the silver staining technique which has been used for the detection of one or more biocomponents fractionated on a support medium. The technique of this invention can bring about marked effects such that the operation time is shortened to a considerably extent, the efficiency of work and operation and the staining ability are improved significantly, and stained profiles can be obtained with sufficiently enhanced contrast.

EXAMPLES

This invention will hereinafter be described in further detail by the following examples. It should however be borne in mind that this invention is not limited whatsoever by the following examples.

EXAMPLE 1

Staining of Serum Protein Fractions

I. Electrophoresis:

Preparation of reagents (1) Support medium:

A commercially-available electrophoretic polyacrylamide gradient gel, "SDS-PAG Plate 4/20" ( trademark ; product of Daiichi Pure Chemicals Co., Ltd.) was used.

(2) Sample treatment solution:

A 0.125 M tris-HCl buffer (pH 6.8) containing 4.3 w/v% of sodium dodecylsulfate, 0.02 w/v% Bromophenol Blue and 30 v/v% of glycerol was prepared.

(3) Samples:

A normal human serum sample diluted fiftyfold in water and 2-fold, 4-fold, 8-fold, 16-fold, 32-fold, 64-fold, 128-fold, 256-fold and 512-fold dilute solutions of the serum sample were separately mixed with an equal amount of the sample treatment solution, followed by the boiling treatment for 5 minutes in boiling water to prepare samples.

(4) Electrophoretic buffer:

A 0.025 M tris-0.192 M glycine buffer (pH 8.4) containing 0.1 w/v% of sodium dodecylsulfate was prepared.

Electrophoretic procedure

After placing the support medium in an electrophoretic bath, the bath was filled with the electrophoretic buffer. The samples were applied in 5 $\mu l$ portions to sample wells of the support medium and were electrophorsed under a constant current of 60 mA for about 1 hour.

II. Silver Staining:

Preparation of reagents (1) First fixing agent:

A solution containing 50 v/v% of methanol and 10 w/v% of acetic acid was prepared.

(2) Second fixing agent:

A solution containing 30 v/v% of methanol, 10 w/v% of acetic acid and 0.0025 w/v% of thiourea was prepared.

(3) Sensitizer:

A solution containing 50 v/v% of methanol, 0.0005 w/v% of dithiothreitol and 0.1 w/v% of glutaraldehyde was prepared.

(4) Silver staining solution:

A solution containing 0.2 w/v% of silver nitrate, 0.14 w/v% of ammonia and 0.2 w/v% of sodium hydroxide was prepared.

(5) Reducing agent:

A solution containing 0.02 w/v% of formaldehyde and 0.005 w/v% of citric acid was prepared.

(6) Terminator:

A solution containing 10 w/v% of citric acid was prepared.

Staining procedure

A support medium which had been subjected to electrophoresis was immersed under shaking for 10 minutes in the first fixing agent and then for 15 minutes in the second fixing agent. After immersing the support medium for 10 minutes in the sensitizer, it was shaken and washed for 5 minutes in deionized water. The support medium was immersed under shaking for 15 minutes in the silver staining solution, and was then shaken and washed three times for 2 minutes each time in deionized water. After immersing under shaking the support medium in the reducing agent until a stained pattern appeared, namely, for about 5 minutes, the terminator was added to terminate the development.

The total time required for the above staining procedure was 66 minutes.

EXAMPLE 2

Staining of Serum Protein Fractions

Preparation of reagents (1) First fixing agent:

Same as Example 1.

(2) Second fixing agent:

A solution containing 30 v/v% of methanol and 10 w/v% of acetic acid was prepared.

(3) Sensitizer:

A solution containing 50 v/v% of methanol, 0.0005 w/v% of dithiothreitol, 0.1 w/v% of glutaraldehyde and 0.00025 w/v% of thiourea was prepared.

(4) Silver staining solution:

Same as Example 1.

(5) Reducing agent:

Same as Example 1.

(6) Terminator:

Staining procedure

Same as Example 1.

EXAMPLE 3

Staining of Serum Protein Fractions

Preparation of reagents (1) First fixing agent:
Same as Example 1.
(2) Second fixing agent:
Same as Example 1.
(3) Sensitizer:
Same as Example 2.
(4) Silver staining solution:
Same as Example 1.
(5) Reducing agent:
Same as Example 1.
(6) Terminator:
Same as Example 1.

Staining procedure

Same as Example 1.

EXAMPLE 4

Staining of Serum Protein Fractions

Preparation of reagents (1) First fixing agent:
A solution containing 50 v/v% of methanol, 10 w/v% of acetic acid and 0.0025 w/v% of thiourea was prepared.
(2) Second fixing agent:
Same as Example 2.
(3) Sensitizer:
Same as Example 1.
(4) Silver staining solution
Same as Example 1.
(5) Reducing agent:
Same as Example 1.
(6) Terminator:
Same as Example 1

Staining procedure

Same as Example 1

EXAMPLE 5

Staining of Serum Protein Fractions

Preparation of reagents (1) First fixing agent:
Same as Example 4.
(2) Second fixing agent:
Same as Example 2.
(3) Sensitizer:
Same as Example 2.
(4) Silver staining solution:
Same as Example 1.
(5) Reducing agent:
Same as Example 1.
(6) Terminator:
Same as Example 1.

Staining procedure

Same as Example 1.

EXAMPLE 6

Staining of Serum Protein Fractions

Preparation of reagents (1) First fixing agent:
Same as Example 1.
(2) Second fixing agent:
Same as Example 1.
(3) Sensitizer:
A solution containing 50 v/v% of methanol, 0.0005 w/v% of dithiothreitol and 0.00025 w/v% of thiourea was prepared.
(4) Silver staining solution:
Same as Example 1.
(5) Reducing agent:
Same as Example 1.
(6) Terminator:
Same as Example 1.

Staining procedure

Same as Example 1.

EXAMPLE 7

Staining of Serum Protein Fractions

Preparation of reagents (1) First fixing agent:
Same as Example 1.
(2) Second fixing agent:
Same as Example 1.
(3) Sensitizer:
A solution containing 50 v/v% of methanol, 0.05 w/v% of glutaraldehyde and 0.00025 w/v% of thiourea was prepared.
(4) Silver staining solution:
Same as Example 1.
(5) Reducing agent:
Same as Example 1.
(6) Terminator:
Same as Example 1.

Staining procedure

Same as Example 1.

EXAMPLE 8

Staining of Serum Protein Fractions

Preparation of reagents (1) First fixing agent:
Same as Example 1.
(2) Second fixing agent:
Same as Example 1.
(3) Sensitizer:
A solution containing 50 v/v% of methanol and 0.00025 w/v% of thiourea was prepared.
(4) Silver staining solution:
Same as Example 1.
(5) Reducing agent:
Same as Example 1.
(6) Terminator:
Same as Example 1.

Staining procedure

Same as Example 1.

EXAMPLE 9

Staining of Serum Protein Fractions

Preparation of reagents (1) First fixing agent:
Same as Example 4.
(2) Second fixing agent:
Same as Example 2.

(3) Sensitizer:
Same as Example 6.
(4) Silver staining solution:
Same as Example 1.
(5) Reducing agent:
Same as Example 1.
(6) Terminator:
Same as Example 1.

Staining procedure

Same as Example 1.

EXAMPLE 10

Staining of Serum Protein Fractions

Preparation of reagents (1) First fixing agent:
Same as Example 4.
(2) Second fixing agent:
Same as Example 2.
(3) Sensitizer:
Same as Example 7.
(4) Silver staining solution:
Same as Example 1.
(5) Reducing agent:
Same as Example 1.
(6) Terminator:
Same as Example 1.

Staining procedure

Same as Example 1.

EXAMPLE 11

Staining of Serum Protein Fractions

Preparation of reagents (1) First fixing agent:
Same as Example 4.
(2) Second fixing agent:
Same as Example 2.
(3) Sensitizer:
Same as Example 8.
(4) Silver staining solution:
Same as Example 1.
(5) Reducing agent:
Same as Example 1.
(6) Terminator:
Same as Example 1.

Staining procedure

Same as Example 1.

EXAMPLE 12

Staining of Serum Protein Fractions

Preparation of reagents (1) Fixing agent:
A solution containing 30 v/v% of methanol, 10 w/v% of acetic acid and 0.0025 w/v% of thiourea was prepared.
(2) Sensitizer:
Same as Example 1.
(3) Silver staining solution:
Same as Example 1.
(4) Reducing agent:
Same as Example 1.
(5) Terminator:
Same as Example 1.

Staining procedure

A support medium which had been subjected to electrophoresis was immersed under shaking for 10 minutes in the fixing agent. The support medium was immersed under shaking for 10 minutes in the sensitizer and was then shaken and washed for 5 minutes in deionized water. The support medium was immersed under shaking for 15 minutes in the silver staining solution, and was then shaken and washed three times for 2 minutes each time in deionized water. After immersing under shaking the support medium in the reducing agent until a stained pattern appeared, namely, for 5 minutes, the terminator was added to terminate the development.

The total time required for the above staining procedure was 50 minutes.

EXAMPLE 13

Staining of Serum Protein Fractions

Preparation of reagents (1) Fixing agent:
Same as Example 12
(2) Sensitizer:
Same as Example 2.
(3) Silver staining solution:
Same as Example 1.
(4) Reducing agent:
Same as Example 1.
(5) Terminator:
Same as Example 1.

Staining procedure

Same as Example 12

Example 14

Staining of Serum Protein Fractions

Preparation of reagents (1) Fixing agent:
A solution containing 30 v/v% of methanol and 10 w/v% of acetic acid was prepared.
(2) Sensitizer:
Same as Example 2.
(3) Silver staining solution
Same as Example 1.
(4) Reducing agent:
Same as Example 1.
(5) Terminator:
Same as Example 1.

Staining procedure

Same as Example 12.

EXAMPLE 15

Staining of Serum Protein Fractions

Preparation of reagents (1) Fixing agent:
Same as Example 14.
(2) Sensitizer:
Same as Example 7
(3) Silver staining solution:
Same as Example 1.
(4) Reducing agent:
Same as Example 1.
(5) Terminator:
Same as Example 1.

Staining procedure

Same as Example 12.

EXAMPLE 16

Staining of Serum Protein Fractions

Preparation of reagents (1) Fixing agent:
Same as Example 14.
(2) Sensitizer:
Same as Example 8.
(3) Silver staining solution:
Same as Example 1.
(4) Reducing agent:
Same as Example 1.
(5) Terminator:
Same as Example 1.

Staining procedure

Same as Example 12.

EXAMPLE 17

Staining of Serum Protein Fractions

Preparation of reagents (1) Fixing agent:
Same as Example 14.
(2) Sensitizer:
Same as Example 6.
(3) Silver staining solution:
Same as Example 1.
(4) Reducing agent:
Same as Example 1.
(5) Terminator:
Same as Example 1.

Staining procedure

Same as Example 12.

EXAMPLE 18

Staining of Serum Protein Fractions

Preparation of reagents (1) First fixing agent:
Same as Example 1.
(1) Second fixing agent:
Same as Example 1.
(3) Sensitizer:
Same as Example 1.
(4) Silver staining solution:
Same as Example 1.
(5) Reducing agent:
A solution containing 0.02 w/v% of formaldehyde, 0.005 w/v% of citric acid and 0.00005 w/v% of sodium thiosulfate was prepared.
(6) Terminator:
Same as Example 1.

Staining procedure

Same as Example 1.

EXAMPLE 19

Staining of Serum Protein Fractions

Preparation of reagents (1) First fixing agent:
Same as Example 1.
(1) Second fixing agent:
Same as Example 2.
(3) Sensitizer:
Same as Example 2.
(4) Silver staining solution:
Same as Example 1.
(5) Reducing agent:
Same as Example 1.
(6) Terminator:
Same as Example 1.

Staining procedure

Same as Example 1.

EXAMPLE 20

Staining of Serum Protein Fractions

Preparation of reagents (1) First fixing agent:
Same as Example 1.
(1) Second fixing agent:
Same as Example 1.
(3) Sensitizer:
Same as Example 2.
(4) Silver staining solution:
Same as Example 1.
(5) Reducing agent:
Same as Example 18.
(6) Terminator:
Same as Example 1.

Staining procedure

Same as Example 1.

EXAMPLE 21

Staining of Serum Protein Fractions

Preparation of reagents (1) First fixing agent:
Same as Example 4.
(2) Second fixing agent:
Same as Example 2.
(3) Sensitizer:
Same as Example 1.
(4) Silver staining solution:
Same as Example 1.
(5) Reducing agent:
Same as Example 18.
(6) Terminator:
Same as Example 1.

Staining procedure

Same as Example 1. After the immersion for 5 minutes, the terminator was added to terminate the development.

The total time required for the above procedure was 50 minutes.

EXAMPLE 22

Staining of Serum Protein Fractions

Preparation of reagents (1) Fixing agent:
Same as Example 12.
(2) Sensitizer:
Same as Example 2.
(3) Silver staining solution:
Same as Example 1.

(4) Reducing agent:
Same as Example 18.
(5) Terminator:
Same as Example 1.

Staining procedure

Same as Example 12.

The total time required for the above staining procedure was 50 minutes.

EXAMPLE 23

Staining of Serum Protein Fractions

Preparation of reagents (1) Fixing agent:
Same as Example 13.
(2) Sensitizer:
Same as Example 7.
(3) Silver staining solution:
Same as Example 1.
(4) Reducing agent:
Same as Example 18.
(5) Terminator:
Same as Example 1.

Staining procedure

Same as Example 12.

EXAMPLE 24

Staining of Serum Protein Fractions

Preparation of reagents (1) Fixing agent:
Same as Example 13.
(2) Sensitizer:
Same as Example 6..
(3) Silver staining solution:
Same as Example 1.
(4) Reducing agent:
Same as Example 18.
(5) Terminator:
Same as Example 1.

Staining procedure

Same as Example 12.

EXAMPLE 25

Staining of Serum Protein Fractions

Preparation of reagents (1) First fixing agent:
Same as Example 1.
(2) Second fixing agent:
Same as Example 2.
(3) Sensitizer:
Same as Example 1.
(4) Silver staining solution:
Same as Example 1.
(5) Reducing agent:
Same as Example 18.
(6) Terminator:
Same as Example 1.

Staining procedure

Same as Example 1.

EXAMPLE 26

Staining of Serum Protein Fractions

Preparation of reagent (1) First fixing agent:
Same as Example 1.
(2) Second fixing agent:
Same as Example 1.
(3) Sensitizer:
Same as Example 1.
(4) Silver staining solution:
A solution containing 0.2 w/v% of silver nitrate, 0.14 w/v% of ammonia and 0.2 w/v% of potassium hydroxide was prepared.
(5) Reducing agent:
Same as Example 1.
(6) Terminator:
Same as Example 1.

Staining procedure

Same as Example 1.

EXAMPLE 27

Staining of Serum Protein Fractions

Preparation of reagent (1) First fixing agent:
Same as Example 1.
(2) Second fixing agent:
Same as Example 2.
(3) Sensitizer:
Same as Example 1.
(4) Silver Staining solution:
A solution containing 0.2 w/v% of silver nitrate, 0.4 w/v% of monomethylamine and 0.2 w/v% of sodium hydroxide was prepared.
(5) Reducing agent:
Same as Example 18.
(6) Terminator:
Same as Example 1.

Staining procedure

Same as Example 1.

COMPARATIVE EXAMPLE

Staining of Serum Protein Fractions

Preparation of reagents (1) First fixing agent:
Same as Example 1.
(2) Second fixing agent:
Same as Example 2.
(3) Sensitizer:
Same as Example 1.
(4) Silver staining solution:
Same as Example 1.
(5) Reducing agent:
Same as Example 1.
(6) Terminator:
Same as Example 1.

Staining procedure

Same as Example 1.

We claim:

1. In a silver staining technique comprising fixing a support medium, which contains a substance to be detected, with a fixing agent, pretreating the thus-fixed support medium with a sensitizer, treating the resultant support medium with a silver staining solution and then developing the thus-treated support medium with a reducing agent, the improvement wherein the fixing agent comprises thiourea, a lower alcohol having 1-4 carbon atoms and an organic acid.

2. The technique of claim 1, wherein the fixing treatment is in two stages.

3. In a silver staining technique comprising fixing a support medium, which contains a substance to be detected, with a fixing agent, pretreating the thus-fixed support medium with a sensitizer, treating the resultant support medium with a silver staining solution and then developing the thus-treated support medium with a reducing agent, the improvement wherein the sensitizer comprises thiourea, dithiothreitol and glutaraldehyde.

4. In a silver staining technique comprising fixing a support medium, which contains a substance to be detected, with a fixing agent, pretreating the thus-fixed support medium with a sensitizer, treating the resultant support medium with a silver staining solution and then developing the thus-treated support medium with a reducing agent, the improvement wherein the reducing agent comprises a thiosulfate, formaldehyde and citric acid.

5. The technique of claim 4, wherein the thiosulfate is sodium thiosulfate.

6. A silver staining kit comprising:

i) a fixing agent comprising a lower alcohol having 1-4 carbon atoms, an organic acid and thiourea;

ii) a sensitizer comprising dithiothreitol and glutaraldehyde;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising formaldehyde and citric acid.

7. A silver staining kit comprising:

i) a fixing agent comprising a lower alcohol having 1-4 carbon atoms and an organic acid;

ii) a sensitizer comprising dithiothreitol, glutaraldehyde and thiourea;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising formaldehyde and citric acid.

8. A silver staining kit comprising:

i) a fixing agent comprising a lower alcohol having 1-4 carbon atoms, an organic acid and thiourea;

ii) a sensitizer comprising dithiothreitol, glutaraldehyde and thiourea;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising formaldehyde and citric acid.

9. A silver staining kit comprising:

i) a fixing agent comprising a lower alcohol having 1-4 carbon atoms and an organic acid;

ii) a sensitizer comprising dithiothreitol and glutaraldehyde;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising a thiosulfate.

10. The silver staining kit of claim 9, wherein the reducing agent additionally comprises formaldehyde and citric acid.

11. A silver staining kit comprising:

i) a fixing agent comprising a lower alcohol having 1-4 carbon atoms, an organic acid and thiourea;

ii) a sensitizer comprising dithiothreitol and glutaraldehyde;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising a thiosulfate.

12. The silver staining kit of claim 11, wherein the reducing agent additionally comprises formaldehyde and citric acid.

13. A silver staining kit comprising:

i) a fixing agent comprising a lower alcohol having 1-4 carbon atoms and an organic acid;

ii) a sensitizer comprising dithiothreitol, glutaraldehyde and thiourea;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising a thiosulfate.

14. The silver staining kit of claim 13, wherein the reducing agent additionally comprises formaldehyde and citric acid.

15. A silver staining kit comprising:

i) a fixing agent comprising a lower alcohol having 1-4 carbon atoms, an organic acid and thiourea;

ii) a sensitizer comprising dithiothreitol, glutaraldehyde and thiourea;

iii) a silver staining solution comprising silver nitrate, a compound represented by $R\text{-}NH_2$ wherein R denotes a hydrogen atom or a monovalent hydrocarbyl group, and a caustic alkali; and iv) a reducing agent comprising a thiosulfate.

16. The silver staining kit of claim 15, wherein the reducing agent additionally comprises formaldehyde and citric acid.

* * * * *